US012762697B2

(12) United States Patent
Chen et al.

(10) Patent No.: US 12,762,697 B2
(45) Date of Patent: Oct. 13, 2026

(54) METHOD AND SYSTEM FOR CALCULATING PARAMETERS IN LARYNX IMAGE WITH ARTIFICIAL INTELLIGENCE ASSISTANCE

(71) Applicant: Changhua Christian Medical Foundation Changhua Christian Hospital, Changhua County (TW)

(72) Inventors: Andy Chen, Taichung City (TW); Acquah Hackman, Changhua County (TW); Mu-Kuan Chen, Changhua County (TW); Chih-Chin Liu, Taichung City (TW)

(73) Assignee: Changhua Christian Medical Foundation Changhua Christian Hospital, Changhua County (TW)

( * ) Notice: Subject to any disclaimer, the term of this patent is extended or adjusted under 35 U.S.C. 154(b) by 332 days.

(21) Appl. No.: 18/512,018

(22) Filed: Nov. 17, 2023

(65) Prior Publication Data

US 2024/0169533 A1 May 23, 2024

(30) Foreign Application Priority Data

Nov. 17, 2022 (TW) ................................. 111143975

(51) Int. Cl.
*G06T 7/00* (2017.01)
*A61B 1/267* (2006.01)
(Continued)

(52) U.S. Cl.
CPC ............ *G06T 7/0012* (2013.01); *A61B 1/267* (2013.01); *G06T 7/11* (2017.01); *G06T 7/13* (2017.01); *G06T 9/00* (2013.01)

(58) Field of Classification Search
CPC .................... G06T 2207/10068; G06T 7/0012
See application file for complete search history.

(56) References Cited

U.S. PATENT DOCUMENTS

2013/0035940 A1* 2/2013 Wan ....................... G06V 40/16 704/258
2023/0186466 A1* 6/2023 Yamamura ................ G06T 7/62
(Continued)

OTHER PUBLICATIONS

Kaluza J, Niebudek-Bogusz E, Malinowski J, Strumillo P, Pietruszewska W. Assessment of Vocal Fold Stiffness by Means of High-Speed Videolaryngoscopy with Laryngotopography in Prediction of Early Glottic Malignancy: Preliminary Report. Cancers ( Basel). Sep. 27, 2022;14(19):4697. (Year: 2022).*
(Continued)

*Primary Examiner* — Gandhi Thirugnanam
(74) *Attorney, Agent, or Firm* — Apex Juris, pllc.; Cera Oh

(57) ABSTRACT

A method for calculating parameters in a larynx image with an artificial intelligence assistance includes training a deep learning object detection software and a deep learning image recognition and segmentation software to extract a glottis image from a larynx image and recognize a membranous glottal gap; after receiving a larynx image, a plurality of larynx images captured frame-by-frame, or a larynx video that is captured when vocal folds are in a phonating state, extracting a glottis image by the deep learning object detection software; recognizing a membranous glottal gap in the glottis image and correspondingly outputting a membranous glottal gap filter by the deep learning image recognition and segmentation software; performing image processing of edge detection and image patching on the membranous glottal gap filter to clearly outline the membranous glottal gap and obtaining a medical parameter of several vocal fold anatomies from the clearly outlined membranous glottal gap.

4 Claims, 12 Drawing Sheets

(51) Int. Cl.

| | |
|---|---|
| ***G06T 7/11*** | (2017.01) |
| ***G06T 7/13*** | (2017.01) |
| ***G06T 9/00*** | (2006.01) |

(56) References Cited

U.S. PATENT DOCUMENTS

2024/0065526 A1* 2/2024 Teramura ......... A61B 1/000094
2024/0169533 A1* 5/2024 Chen .......................... G06T 9/00
2025/0017460 A1* 1/2025 Sun ...................... A61B 1/2673

OTHER PUBLICATIONS

A. Hamad, M. Haney, T. E. Lever and F. Bunyak, "Automated Segmentation of the Vocal Folds in Laryngeal Endoscopy Videos Using Deep Convolutional Regression Networks," 2019 IEEE/CVF Conference on Computer Vision and Pattern Recognition Workshops (CVPRW), Long Beach, CA, USA, 2019, pp. 140-148 (Year: 2019).*

Kist AM, Gómez P, Dubrovskiy D, Schlegel P, Kunduk M, Echternach M, Patel R, Semmler M, Bohr C, Dürr S, Schützenberger A, Döllinger M. A Deep Learning Enhanced Novel Software Tool for Laryngeal Dynamics Analysis. J Speech Lang Hear Res. Jun. 4, 2021;64(6). (Year: 2021).*

Sakthivel S, Prabhu V. Optimal Deep Learning-Based Vocal Fold Disorder Detection and Classification Model on High-Speed Video Endoscopy. J Healthc Eng. 2022. (Year: 2022).*

Search Report for TW111143975, Issued on Apr. 14, 2023, Total of 1 page.

Kist AM, Gómez P, Dubrovskiy D, Schlegel P, Kunduk M, Echternach M, Patel R, Semmler M, Bohr C, Dürr S, Schützenberger A, Döllinger M. A Deep Learning Enhanced Novel Software Tool for Laryngeal Dynamics Analysis. J Speech Lang Hear Res. Jun. 4, 2021;64(6):1889-1903. doi: 10.1044/2021_JSLHR-20-00498. Epub May 17, 2021. PMID: 34000199.

* cited by examiner

METHOD AND SYSTEM FOR CALCULATING PARAMETERS IN LARYNX IMAGE WITH ARTIFICIAL INTELLIGENCE ASSISTANCE

BACKGROUND OF THE INVENTION

Technical Field

The present invention relates generally to an artificial intelligence assisted computation in smart medical field, and more particularly to a method and a system for reading a larynx image and calculating parameters with an artificial intelligence assistance.

Description of Related Art

Normalized glottal gap area (NGGA) is an important medical parameter adapted to evaluate a phonation condition of vocal folds in clinical researches of Phoniatrics. In order to obtain such medical parameter, firstly a larynx image is obtained by Laryngeal stroboscopy or Flexible endoscopy; then a glottal gap is marked in the larynx image and a glottal gap area is calculated; after a length of a vocal fold is measured, the normalized glottal gap area is obtained by manually substituting the aforementioned data into the formula "(the glottal gap area/square of the length of the vocal fold)×100".

The concept of the normalized glottal gap area was first mentioned in the publication by Omoril in 1996 and is extensively cited in subsequent Phoniatrics medical publications. However, the normalized glottal gap area is calculated by firstly downloading the larynx image to a computer and manually marking the glottal gap in the larynx image; then the glottal gap area is estimated by using an area measuring function of an image processing software, such as ImageJ, so that the glottal gap area in the larynx image is acquired. As such medical parameter is obtained by manually marking the glottal gap in the larynx image and the subsequent calculation of the area of the marked region by using the image processing software is time-consuming, the value of the aforementioned method for obtaining the medical parameter is limited in clinical practice.

BRIEF SUMMARY OF THE INVENTION

In view of the above, the primary objective of the present invention is to provide an object detection technique by an artificial intelligence, wherein after recognizing features of vocal folds in a medical image or a medical video and extracting a glottis image, edges and region of a glottis are marked by artificial intelligence image recognition and segmentation technique and hence the values of medical features are obtained, thereby assisting doctors in quantitatively evaluating the vocal fold condition.

The present invention provides a method for calculating parameters in a larynx image with an artificial intelligence assistance, including: training a model: training a deep learning object detection software by a plurality of larynx images with a manually marked glottis image region to extract a glottis image from a larynx image received and training a deep learning image recognition and segmentation software by a plurality of glottis images with a manually marked membranous glottal gap to recognize a membranous glottal gap in a glottis image received; the membranous glottal gap includes structural features of a left vocal process, a right vocal process, and an anterior commissure;

receiving a larynx image: receiving a larynx image, a plurality of larynx images captured frame-by-frame, or a larynx video that is captured when vocal folds are in a phonating state; recognizing a glottis image: extracting at least one glottis image from the larynx image, the plurality of larynx images, or the larynx video by the deep learning object detection software; recognizing a membranous glottal gap in the glottis image: recognizing a membranous glottal gap in the at least one glottis image by the deep learning image recognition and segmentation software and outputting at least one membranous glottal gap filter corresponding to the at least one glottis image by the deep learning image recognition and segmentation software; and obtaining a medical parameter: performing image processing of edge detection and image patching on the at least one membranous glottal gap filter to clearly outline a membranous glottal gap in the at least one membranous glottal gap filter and obtaining a medical parameter of a plurality of vocal fold anatomies from the clearly outlined membranous glottal gap in the at least one membranous glottal gap filter.

The present invention further provides a system for calculating parameters in a larynx image with an artificial intelligence assistance, including an input unit, a processing unit, and an output unit. The input unit receives a medical image. The medical image includes a larynx image, a plurality of larynx images captured frame-by-frame, or a larynx video that is captured when vocal folds are in a phonating state. The processing unit is in signal connection with the input unit and is configured to perform a deep learning algorithm to compute the medical image received by the input unit. The deep learning algorithm includes a deep learning object detection software and a deep learning image recognition and segmentation software.

The processing unit extracts at least one glottis image from the medical image by the deep learning object detection software. The processing unit recognizes a membranous glottal gap in the at least one glottis image by the deep learning image recognition and segmentation software and outputs at least one membranous glottal gap filter corresponding to the at least one glottis image. The processing unit performs image processing of edge detection and image patching on the at least one membranous glottal gap filter to clearly outline a membranous glottal gap in the at least one membranous glottal gap filter. At least one medical parameter, which corresponds to at least one vocal fold anatomy, is obtained from the clearly outlined membranous glottal gap in the at least one membranous glottal gap filter and at least one vocal fold anatomy mark is added to a position of the medical image corresponding to the at least one medical parameter. The output unit is in signal connection with the processing unit. The output unit receives the medical image having the at least one vocal fold anatomy mark and the at least one medical parameter from the processing unit and outputs the medical image and the at least one medical parameter as a medical parameter and image report.

With the aforementioned design, by recognizing the vocal fold anatomies and features in the medical image, such as the larynx image and the glottis image, by the artificial intelligence and performing rapid or immediate computation, the medical parameters, such as the normalized membranous glottal gap area and the amplitude of vocal fold vibration, are obtained, thereby assisting in evaluating the vocal fold condition. As the conventional way is to manually determine the position and the region of the vocal fold anatomies upon obtaining image information, such as incomplete adduction of vocal folds and mucosal wave, from the larynx images captured frame-by-frame by Laryngeal stroboscopy, the determination result of the conventional way is relatively subjective and is hard to be normalized. The present invention prevents the aforementioned problems of the conventional way.

BRIEF DESCRIPTION OF THE SEVERAL VIEWS OF THE DRAWINGS

The present invention will be best understood by referring to the following detailed description of some illustrative embodiments in conjunction with the accompanying drawings, in which.

DETAILED DESCRIPTION OF THE INVENTION

Figure 1:
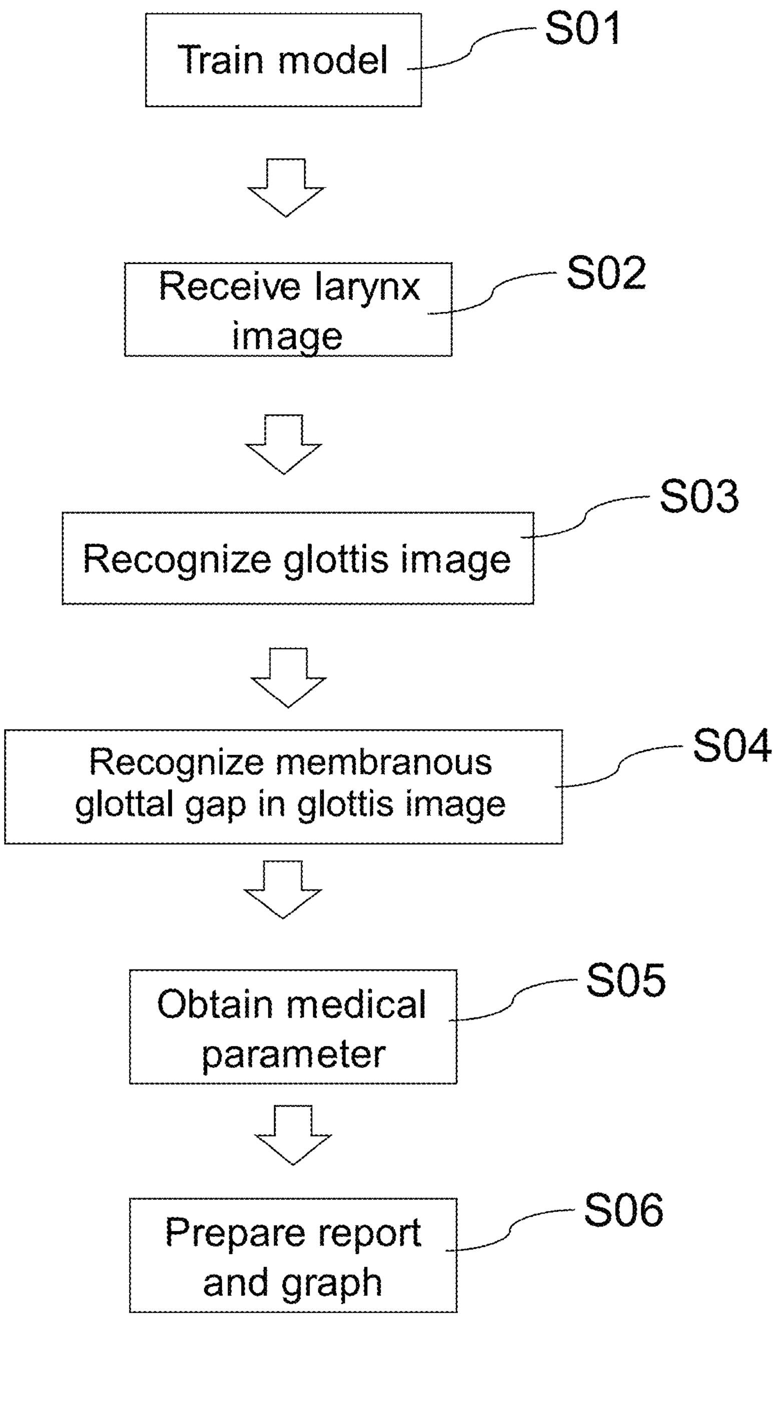
FIG. 1 is a flowchart of the method for calculating the parameters in the larynx image with the artificial intelligence assistance according to an embodiment of the present invention.
Figure 2A:
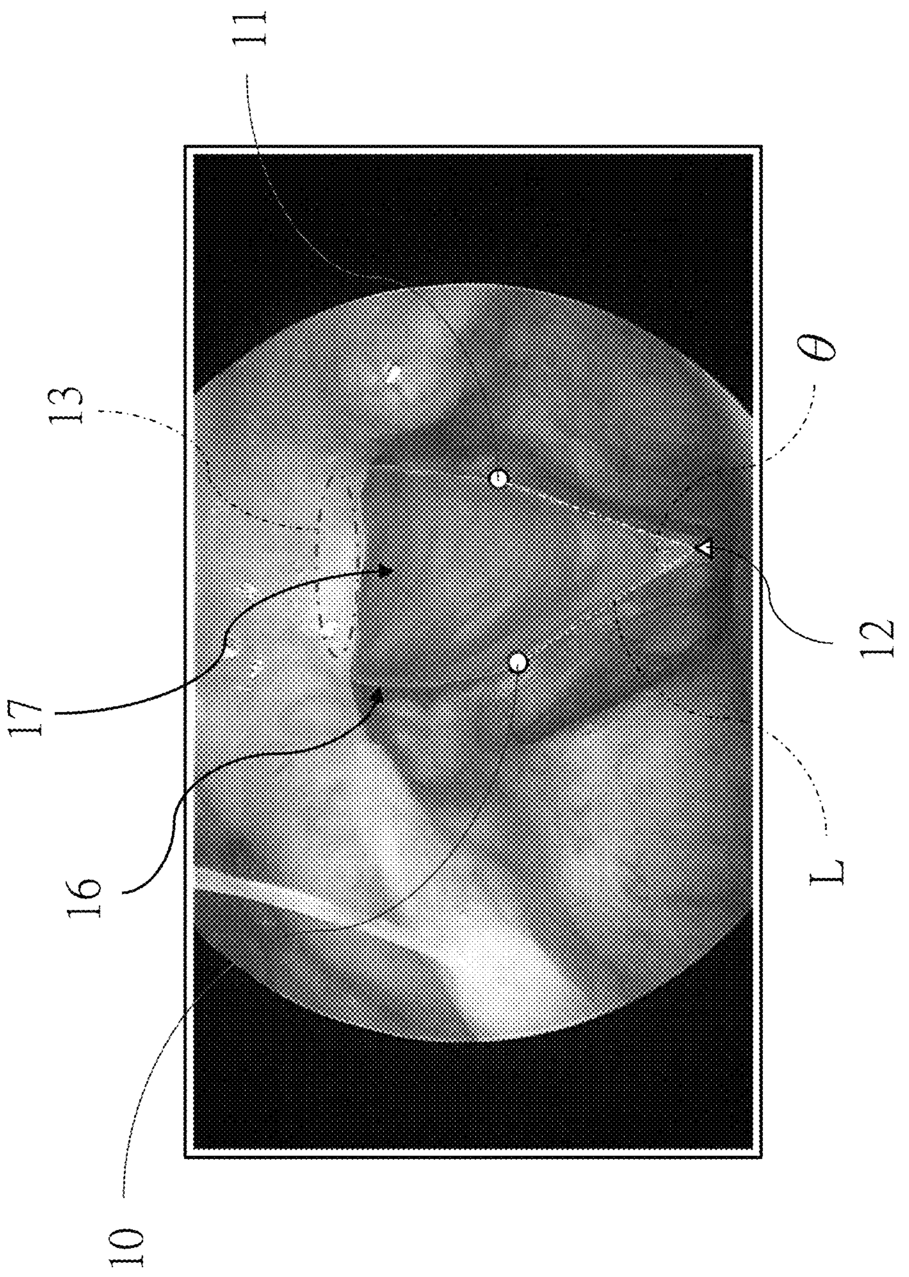
FIG. 2A to FIG. 2C are schematic views, showing the larynx image during vocal fold abduction.

FIG. 1 is a flowchart of a method for calculating parameters in a larynx image with an artificial intelligence assistance according to an embodiment of the present invention, wherein the method includes steps of:

Step S01: train a model: FIG. 2A and FIG. 2B are respectively a larynx image showing vocal folds are abducted, wherein important vocal fold anatomies include a left vocal process 10, a right vocal process 11, an anterior commissure 12, a posterior commissure 13, a vocal fold length L, a glottis angle θ, and a glottis 16. The glottis 16 has a gap between the anterior commissure 12 and the posterior commissure 13 and allowing breathing air to pass through, wherein the gap refers to a glottal gap 17. The vocal fold length L is a straight-line length from the left vocal process 10 to the anterior commissure 12 or from the right vocal process 11 to the anterior commissure 12. The glottis angle θ is an angle formed between a linkage of the left vocal process 10 and the anterior commissure 12 and a linkage of the right vocal process 11 and the anterior commissure 12. An opening degree of the glottis 16 could be acquired by the glottis angle θ.

Figure 2C:
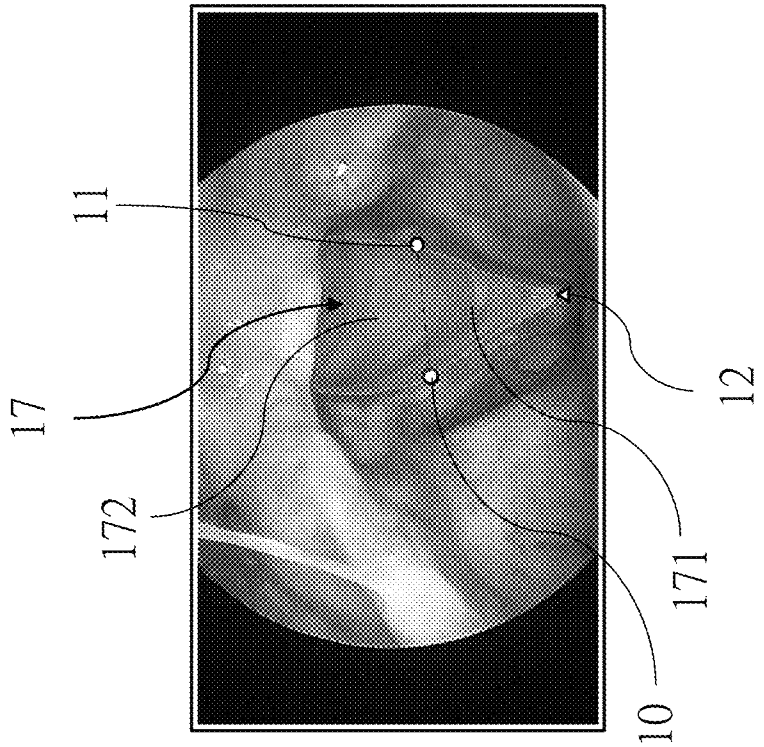
Figure 2B:
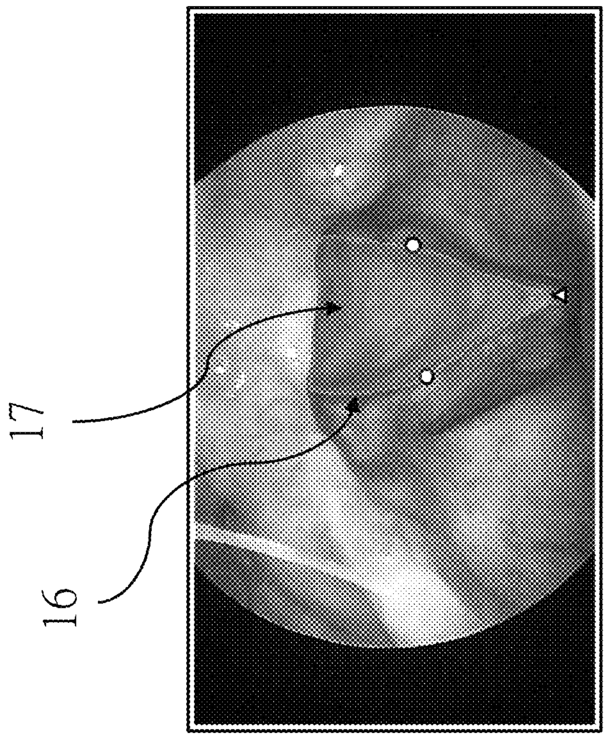

As shown in FIG. 2C, an area of the glottal gap 17 is an area between the left vocal process 10 and the right vocal process 11. The glottal gap 17 is divided into a membranous glottal gap 171 adjacent to the anterior commissure 12 and a cartilaginous glottal gap 172 away from the anterior commissure 12. In conventional publications and techniques, a normalized glottal gap area of the glottal gap 17 is used to evaluate the vocal fold condition. However, the area of the glottal gap 17 is easily affected by the cartilaginous glottal gap 172, which has a larger area but has no significant effect on phonation. Therefore, the present invention makes use of the membranous glottal gap 171 to calculate a normalized membranous glottal gap as a medical parameter, thereby providing a more accurate and precise value for doctors to quantitatively evaluate the vocal fold condition.

Figure 3:
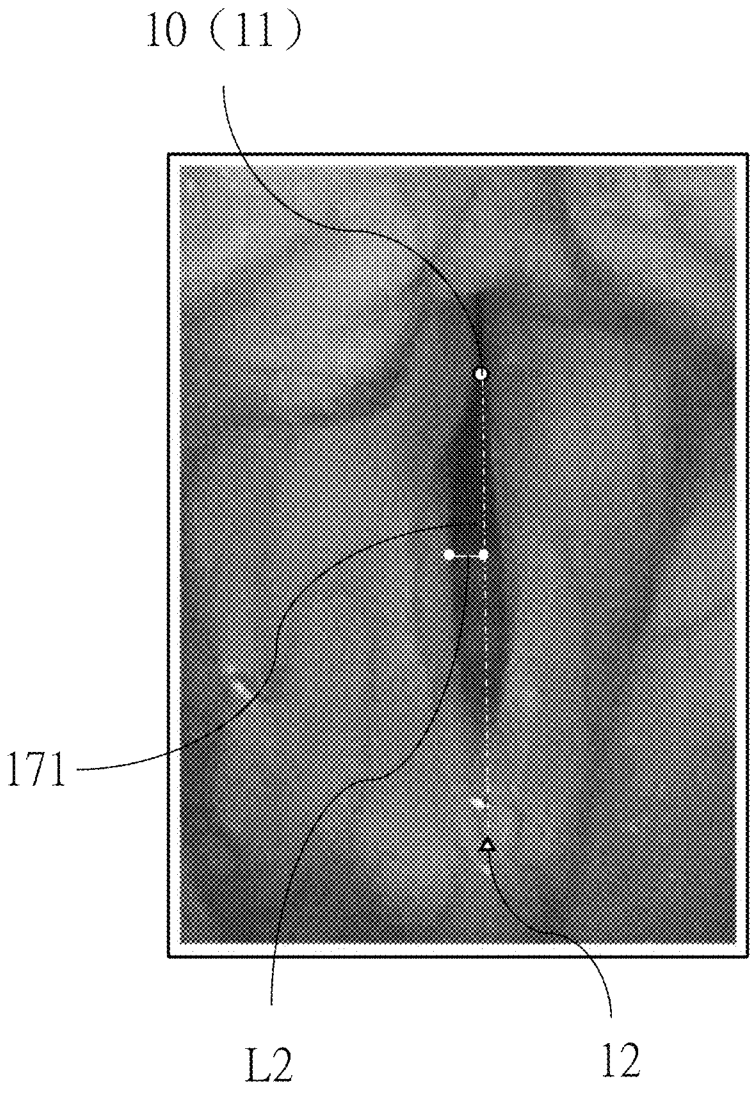
FIG. 3 is a schematic view, showing the larynx image of the vocal folds in the phonating state.

FIG. 3 is a glottis image showing that the vocal folds are adducted to adduct the left vocal process 10 and the right vocal process 11 when the vocal folds are in a phonating state, wherein the larynx image is obtained by capturing the corresponding glottis 16 from the larynx image. The larynx image or the larynx video obtained by Laryngeal stroboscopy or Flexible endoscopy is taken when the vocal folds are in the phonating state. At that time, air stream passes through the narrow glottis, so that a vocal fold mucosa generates a wave-like mucosal wave to produce voice. By capturing images frame-by-frame by using Laryngeal stroboscopy or taking video, larynx images in time order are obtained. Referring to FIG. 2A, FIG. 2C, and FIG. 3, a phonating function of a patient is evaluated by a normalized membranous glottal gap area of the membranous glottal gap 171 and an amplitude of vocal fold vibration L1 of different vocal fold shapes when the vocal folds perform the mucosal wave in the phonating state, wherein the amplitude of vocal fold vibration L1 a longest distance from the linkage of the left vocal process 10 (or the right vocal process 11) and the anterior commissure 12 during vocal fold adduction to a side edge of the membranous glottal gap 171 in a direction perpendicular to the linkage of the left vocal process 10 (or the right vocal process 11) and the anterior commissure 12. Continuous states of the vocal folds performing the mucosal wave could be determined by the amplitude of vocal fold vibration L1 at different time.

Figure 4A:
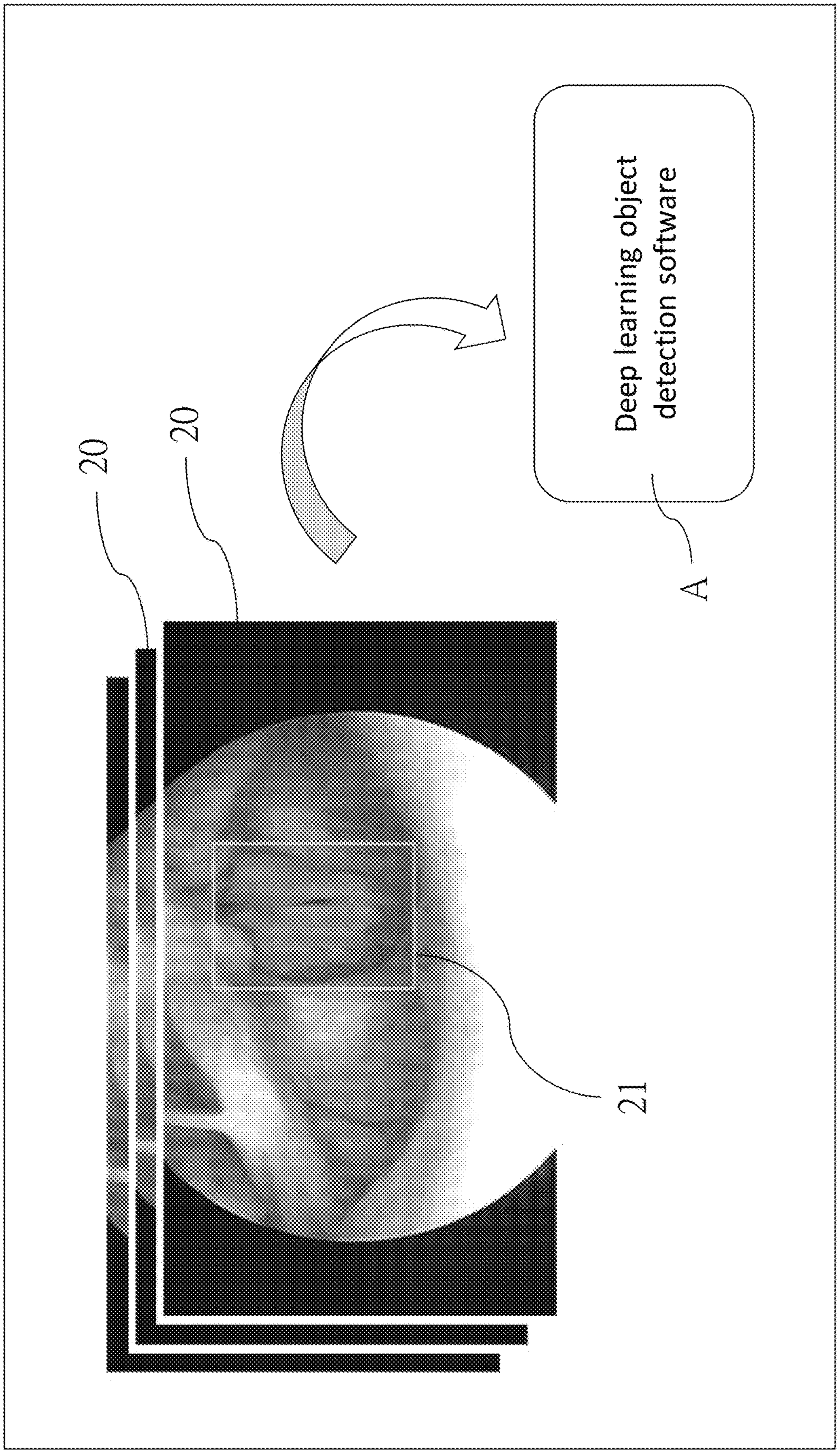
FIG. 4A and FIG. 4B are schematic views of training the model according to the embodiment of the present invention.

Referring to FIG. 4A, during performing Step S01 of training a model, a deep learning object detection software A is trained by a plurality of larynx image 20 with a glottis image region, which is manually marked. In the current embodiment, the deep learning object detection software A is YOLO. The deep learning object detection software A extracts a glottis image 21 from a larynx image 20 received. A deep learning image recognition and segmentation software B is trained by a plurality of glottis images 21 with a membranous glottal gap 171, which is manually marked. In the current embodiment, the deep learning image recognition and segmentation software B is U-Net. The deep learning image recognition and segmentation software B recognizes a membranous glottal gap 171 in a glottis image 21 received. A periphery of the membranous glottal gap 171 includes structural features of the left vocal process 10, the right vocal process 11, and the anterior commissure 12, wherein the structural features surrounding the membranous glottal gap 171 are marked along with training the deep learning image recognition and segmentation software B, so that that deep learning image recognition and segmentation software B could also recognize the structural features included by the membranous glottal gap 171.

Step S02: receive a larynx image: a medical image of a larynx in the phonating state is received, wherein the medical image includes a larynx image, a plurality of larynx images captured frame-by-frame, or a larynx video that is captured when the vocal folds are in the phonating state. In the current embodiment, a plurality of larynx images captured frame-by-frame is used as an example.

Step S03: recognize a glottis image: referring to FIG. 4A, the trained deep learning object detection software A extracts a glottis image 21 from each of the larynx images

Figure 5A:
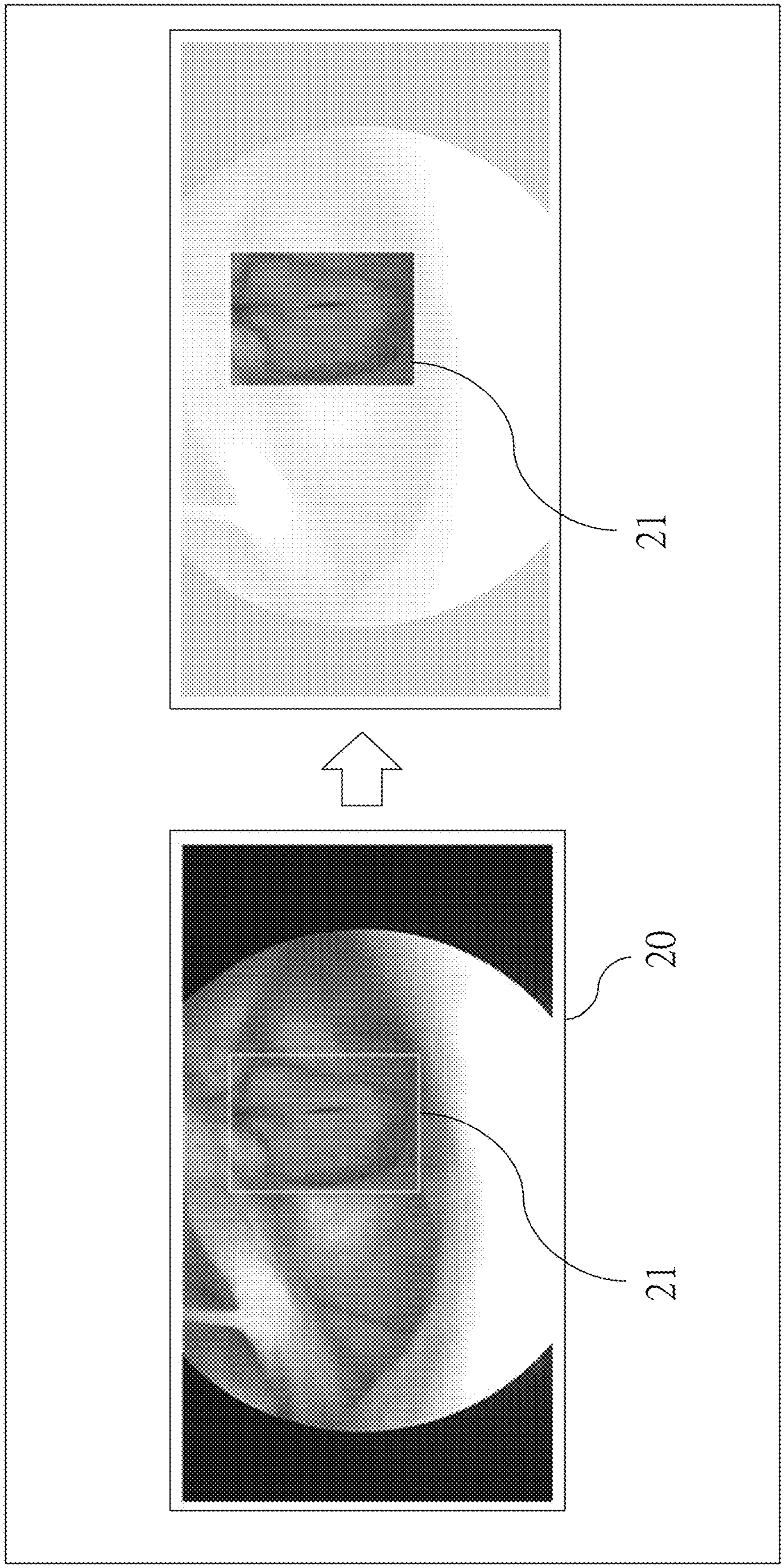
FIG. 5A to FIG. 5D are schematic views of recognizing the glottis image according to the embodiment of the present invention.
Figure 5B:
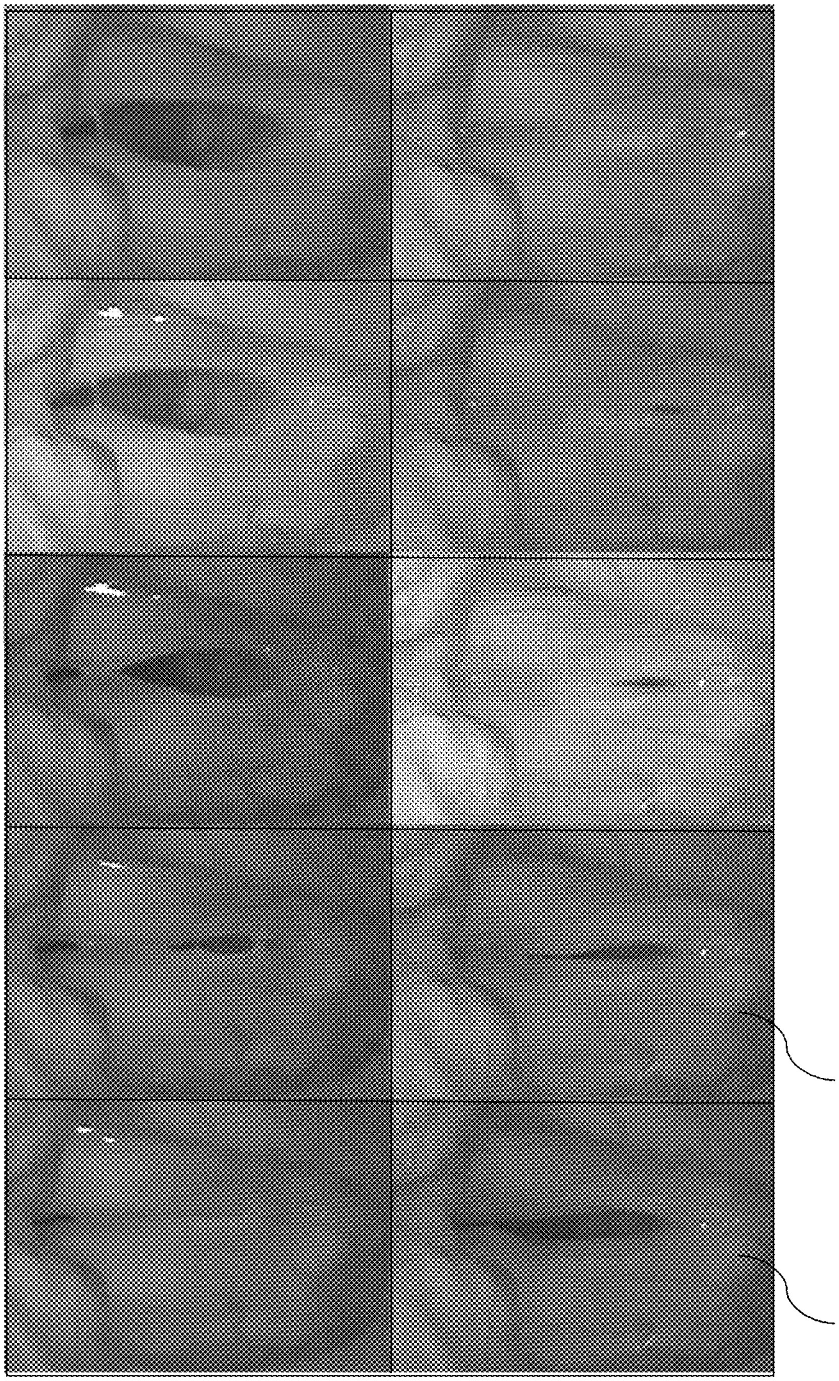

20, so that a plurality of glottis images 21 corresponding to the larynx images 20 are obtained as shown in FIG. 5A and FIG. 5B. In other embodiments, a larynx image 20 or a plurality of larynx images 20 could be received, and the deep learning object detection software A extracts a glottis image 21 from the larynx image 20 or from each of the plurality of larynx images 20; alternatively, a larynx video could be received; the deep learning object detection software A extracts a plurality of larynx images 20 from the larynx video according to the time order, and a glottis image 21 is extracted from each of the plurality of the larynx images 20, so that a plurality of glottis images 21 corresponding to the plurality of larynx images 20 are obtained.

Figure 4B:
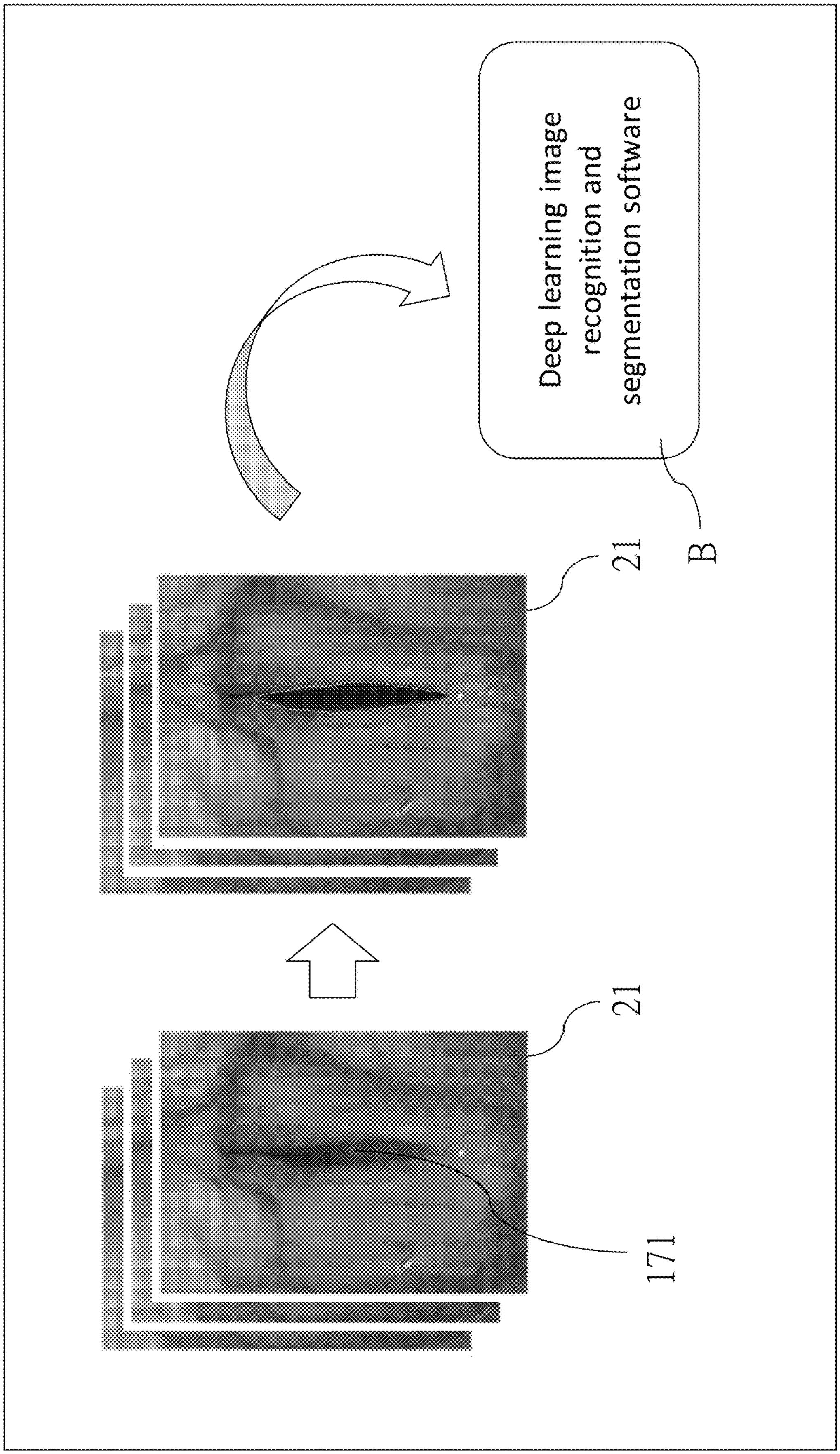
Figure 5C:
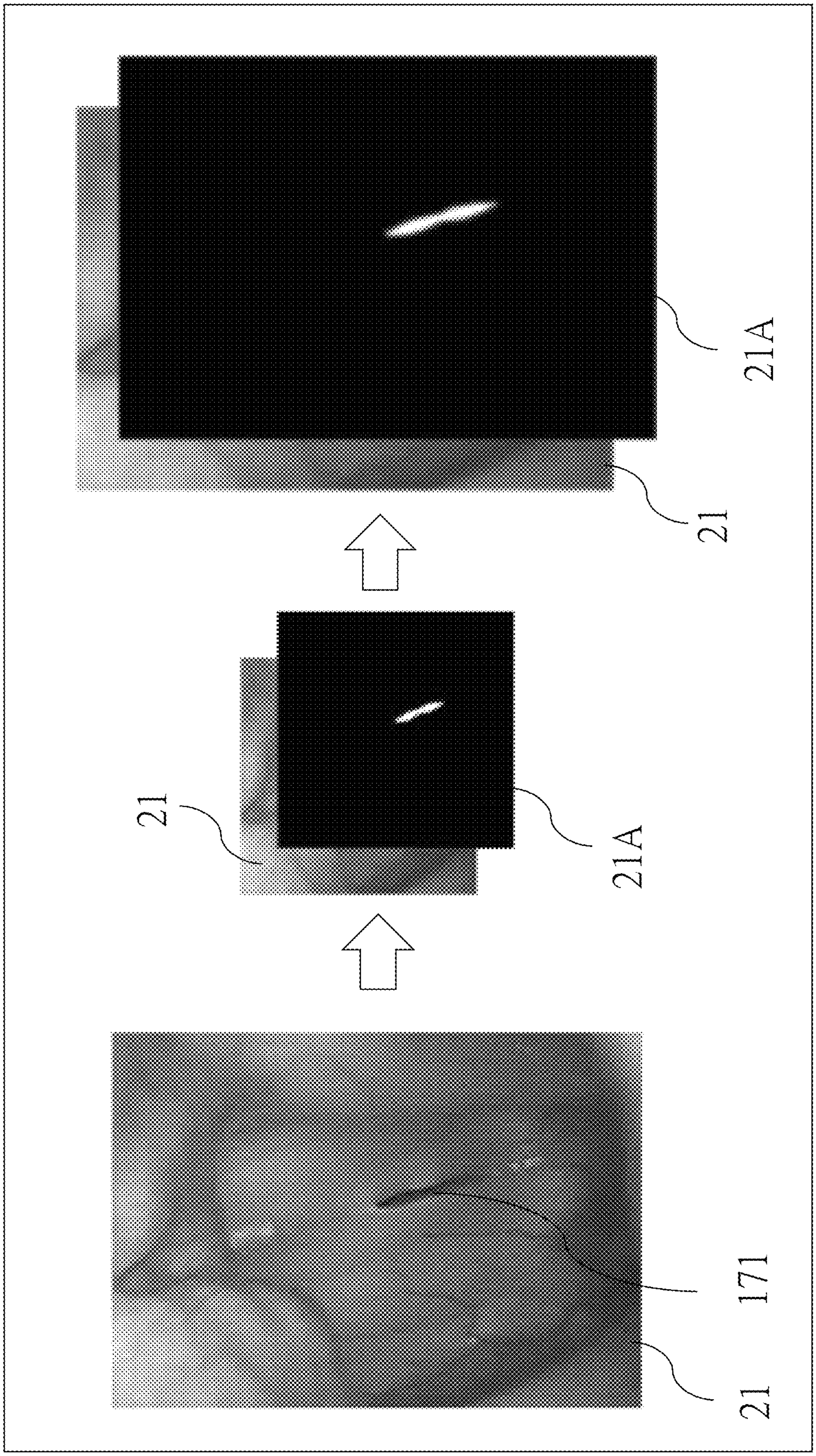

Step S04: recognize a membranous glottal gap in the glottis image: referring to FIG. 4B, the trained deep learning image recognition and segmentation software B respectively recognize a membranous glottal gap 171 in the plurality of glottis images 21 and outputs a membranous glottal gap filter 21A corresponding to one of the glottis images 21 as shown in FIG. 5C, so that a plurality of membranous glottal gap filters 21A corresponding to the plurality of glottis images 21 are obtained. In other embodiments, the deep learning image recognition and segmentation software B could recognize a membranous glottal gap 171 in a glottis image 21 or a membranous glottal gap 171 in a plurality of glottis images 21 and output a membranous glottal gap filter 21A corresponding to the glottis image 21 (the glottis images 21), so that a membranous glottal gap filter 21A corresponding to the glottis image 21 or a plurality of membranous glottal gap filters 21A corresponding to the plurality of glottis images 21 is obtained. In other embodiments, the deep learning object detection software A and the deep learning image recognition and segmentation software B in the present invention that are configured to perform training the model (Step S01), receiving a larynx image (Step S02), recognizing a glottis image (Step S03), and recognizing a membranous glottal gap of the glottis image (Step S04) are not limited to YOLO and U-Net, but could be other deep learning artificial intelligence models having the same functions.

Figure 5D:
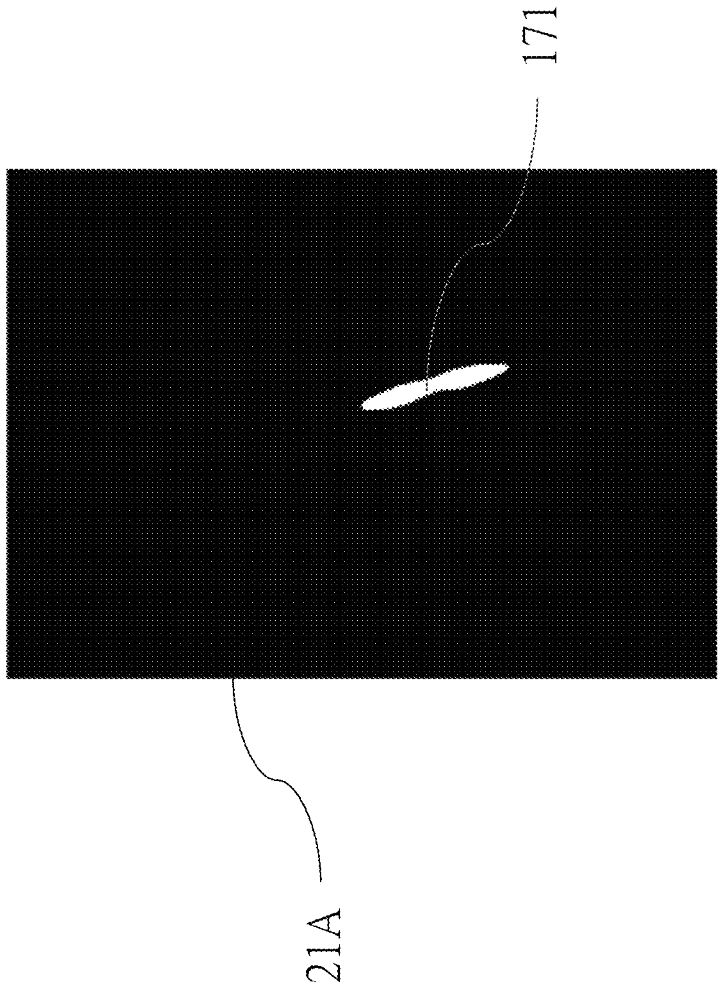

Step S05: obtain a medical parameter: image processing of edge detection and image patching is performed on the membranous glottal gap filter 21A. As shown in FIG. 5D, the membranous glottal gap 171 in each of the membranous glottal gap filters 21A is clearly outlined. A medical parameter of a plurality of vocal fold anatomies is obtained from the clearly outlined membranous glottal gap 171 in each of the membranous glottal gap filters 21A. The medical parameter includes the normalized membranous glottal gap area of the membranous glottal gap 171 and the amplitude of vocal fold vibration L1, but not limited thereto. The value of the medical parameter assists doctors to quantitatively evaluate the vocal fold condition in practice.

The way to obtain the normalized membranous glottal gap area is to calculate the membranous glottal gap area of each of the glottis images 21 from the clearly outlined membranous glottal gap 171 of each of the membranous glottal gap filters 21A and to obtain the vocal fold length L from the same clearly outlined membranous glottal gap 171. The vocal fold length L is a straight-line distance from the left vocal process 10 to the anterior commissure 12 or from the right vocal process 11 to the anterior commissure 12. The membranous glottal gap area and the vocal fold length L are substituted into the formula "the membranous glottal gap area/the square of the vocal fold length)×100", so that the normalized membranous glottal gap area (NMGGA) is calculated.

Additionally, the way to obtain the amplitude of vocal fold vibration L1 is to mark the linkage of the left vocal process 10 (the right vocal process 11) and anterior commissure 12 during vocal fold adduction in the clearly outlined membranous glottal gap 171 of the membranous glottal gap filters 21A and to calculate the longest distance from the side edge of the membranous glottal gap 171 to the linkage of the left vocal process 10 (the right vocal process 11) and anterior commissure 12 in a direction perpendicular to the linkage.

Figure 6:
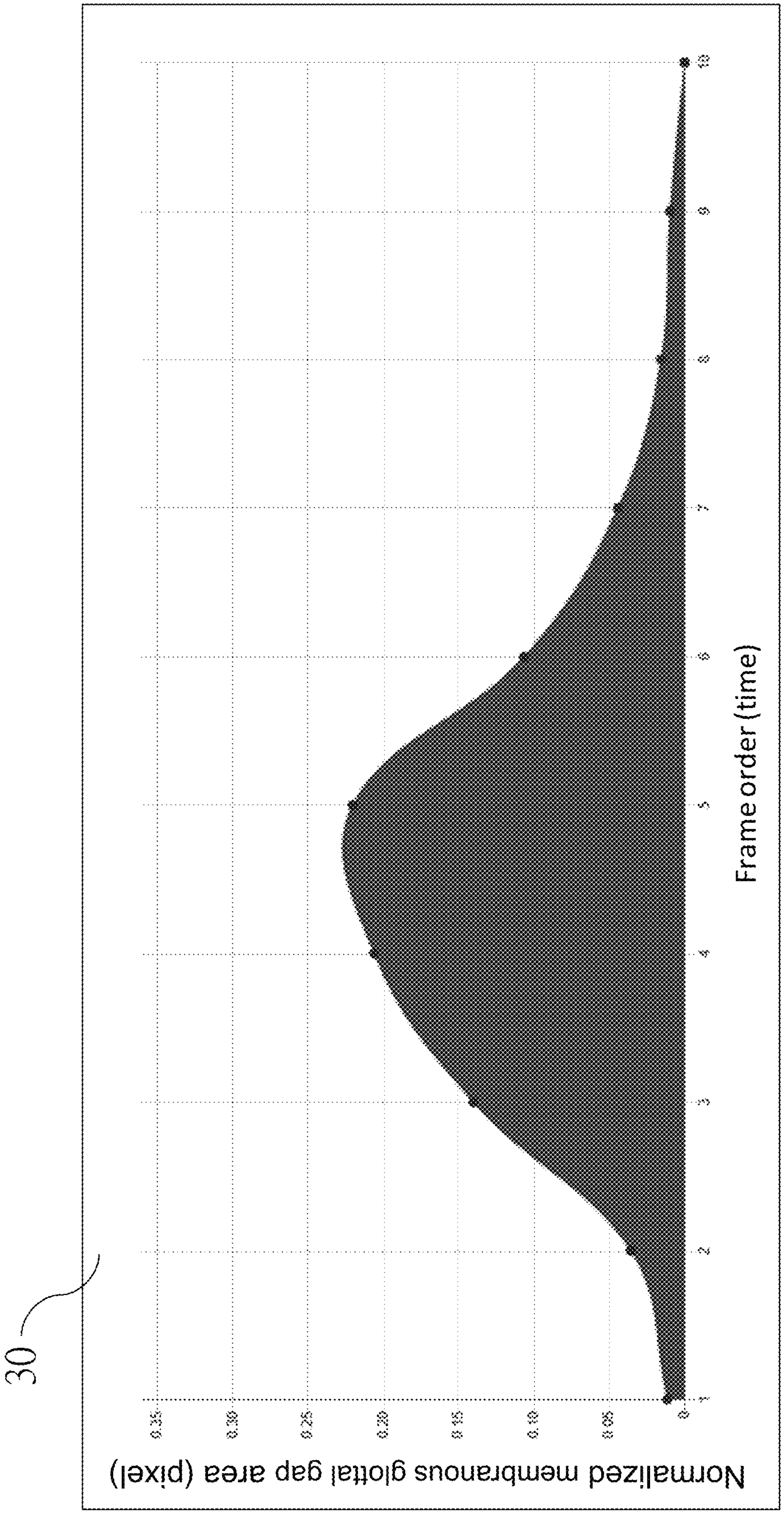
FIG. 6 is a schematic view of the graph according to the embodiment of the present invention.
Figure 7:
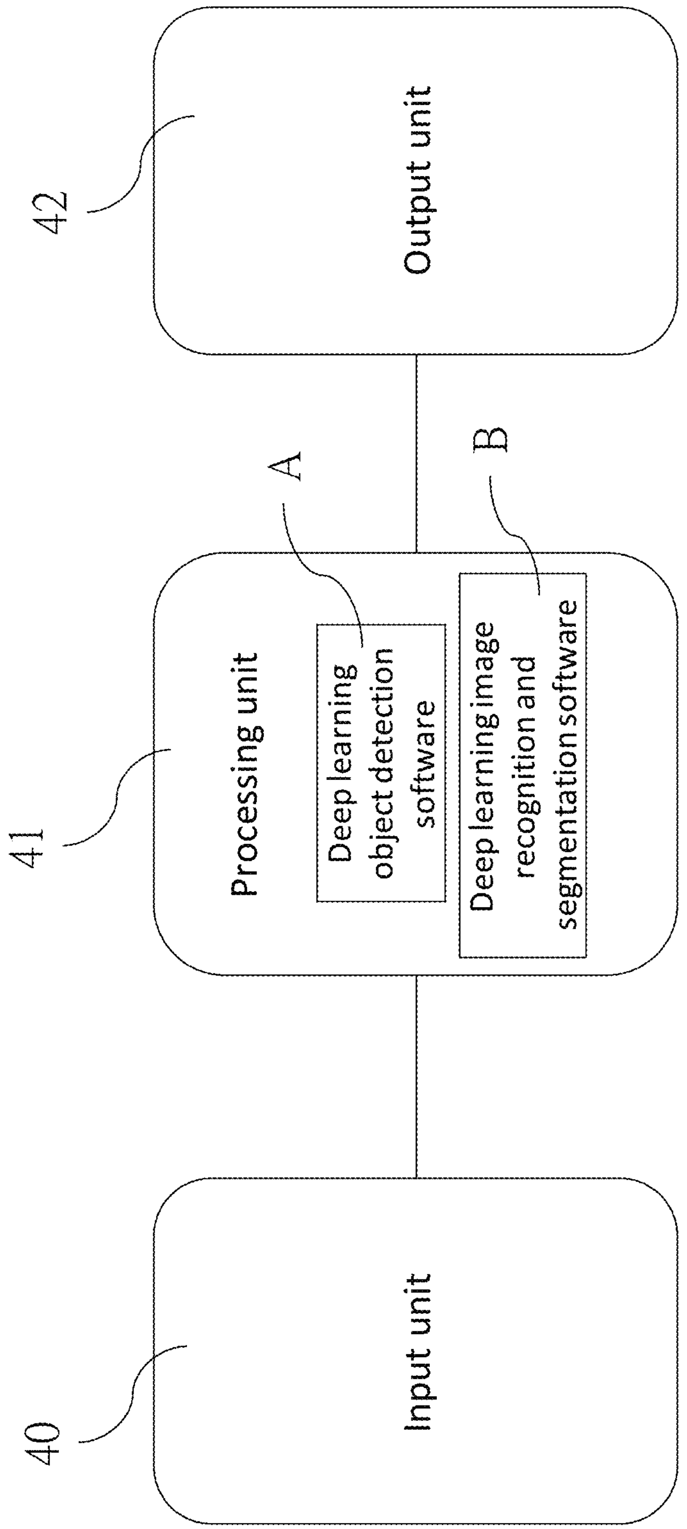
FIG. 7 is a block diagram of the system for calculating the parameters in the larynx image with the artificial intelligence assistance according to an embodiment of the present invention.

Step S06: prepare a report and a graph: after obtaining the medical parameter in Step S05, a graph 30 is prepared with the time or the frame order as a horizontal axis and the normalized membranous glottal gap area as a vertical axis as shown in FIG. 6, wherein the graph 30 is configured to assist in evaluating the vocal fold condition. Step S06 could further add at least one vocal fold anatomy mark corresponding to the medical parameter to the medical image of the glottis images 21 or the larynx images 20. For example, a vocal fold anatomy mark corresponding to the amplitude of vocal fold vibration L1 is added to the glottis images 21; the graph 30, the glottis images 21 having the at least one vocal fold anatomy mark, and the value of the medical parameter corresponding to the glottis images 21 are output as a medical parameter and image report.

The medical parameter in the medical parameter and image report could be one or plural. As the data of the medical parameters is obtained upon performing obtaining the medical parameter (Step S05), Step S06 could be selectively performed. Step S06 is configured to output the medical parameter and medical image obtained in obtaining the medical parameter (Step S05) as a readable and user-friendly report.

In the current embodiment, the deep learning image recognition and segmentation software B is U-net. Therefore, in Step S04 of recognizing a membranous glottal gap of the glottis image, during recognizing the glottal gap 171 by using U-Net, the glottis images are required to be compressed into the glottis images 21 in small size, such as 128 pixels×128 pixels, in advance as shown in FIG. 5C; then U-net (the deep learning image recognition and segmentation software B) respectively recognizes the membranous glottal gap 171 in the glottis images 21 in small size and outputs the membranous glottal gap filters 21A in small size (128 pixels×128 pixels) corresponding to the glottis images 21 in small size; afterwards, U-net (the deep learning image recognition and segmentation software B) restores the membranous glottal gap filters 21A into the membranous glottal gap filters 21A in original size and outputs the membranous glottal gap filters 21A in original size of 384 pixels×540 pixels for subsequently performing image processing of edge detection and image patching.

The present invention further provides a system for calculating parameters in a larynx image with an artificial intelligence assistance. Referring to FIG. 2A to FIG. 4B and FIG. 7, the system is a computer system and includes an input unit 40, a processing unit 41, and an output unit 42. The system is configured to perform the aforementioned method for calculating parameters in the larynx image with the artificial intelligence assistance.

The input unit 40 could be an input interface, a card reader, or a network card and is configured to receive a medical image, wherein the medical image includes a larynx image 20, a plurality of larynx images 20 captured frame-by-frame, or a larynx video that is taken when the vocal folds are in the phonating state.

The processing unit 41 includes a computing, controlling, and memory module. The processing unit 41 is in signal connection with the input unit 40 to receive the medical image. The processing unit 41 perform a deep learning algorithm to compute the medical image received from the input unit 40. The deep learning algorithm includes a deep learning object detection software A and a deep learning image recognition and segmentation software B. In the current embodiment, the deep learning object detection software A is YOLO and is trained by a plurality of larynx images 20 with a manually marked glottis image region; the deep learning image recognition and segmentation software B is U-Net and is trained by the plurality of glottis images 21 with a manually marked membranous glottal gap 171.

The processing unit 41 performs Step S03 of recognizing a glottis image. As shown in FIG. 5A, the deep learning object detection software A extracts a glottis image 21 or a plurality of glottis images 21 from the larynx image 20, the plurality of larynx images 20, or the larynx video. The processing unit 41 preforms Step S04 of recognizing a membranous glottal gap of the glottis image. As shown in FIG. 5C, the deep learning image recognition and segmentation software B recognizes the membranous glottal gap 171 in the glottis image 21 or the plurality of glottis images 21 and outputs a membranous glottal gap filter 21A (a plurality of membranous glottal gap filters 21A) corresponding to the glottis image(s) 21. As shown in FIG. 5D, the processing unit 41 perform image processing of edge detection and image patching on the membranous glottal gap filter(s) 21A by an image processing software to clearly outline the membranous glottal gap 171 in the membranous glottal gap filter(s) 21A. The processing unit 41 performs Step S05 of obtaining a medical parameter. At least one medical parameter, which corresponds to at least one vocal fold anatomy, is obtained from the clearly outlined membranous glottal gap 171 in the membranous glottal gap filter(s) 21A. Upon performing Step S06 of preparing a report and a graph, at least one vocal fold anatomy mark is added to a position of the medical image corresponding to the at least one medical parameter.

The output unit 42 could be an output interface, a printer, or a display screen and is in signal connection with the processing unit 41. The output unit 42 receives the at least one medical parameter and the medical image having the at least one vocal fold anatomy mark from the processing unit 41, wherein the at least one medical parameter includes the normalized membranous glottal gap area of the membranous glottal gap 171 or the amplitude of vocal fold vibration L1. The output unit 42 performs Step S06 of preparing a report and a graph. The output unit 42 output the medical image, such as the glottis image(s) 21 having the at least one vocal fold anatomy mark, and the value of the at least one medical parameter corresponding to the glottis image(s) 21 as a medical parameter and image report. As shown in FIG. 6, the medical parameter and image report could further include the graph 30, wherein the graph 30 is a coordinate graph with the frame order as the horizontal axis and the normalized membranous glottal gap area as the vertical axis.

It must be pointed out that the embodiments described above are only some preferred embodiments of the present invention. All equivalent structures which employ the concepts disclosed in this specification and the appended claims should fall within the scope of the present invention.

What is claimed is:

1. A method for calculating parameters in a larynx image with an artificial intelligence assistance, comprising:

training a deep learning object detection software by a plurality of larynx images with a manually marked glottis image region to extract a glottis image from a larynx image received and training a deep learning image recognition and segmentation software by a plurality of glottis images with a manually marked membranous glottal gap to recognize a membranous glottal gap in a glottis image received; the membranous glottal gap includes structural features of a left vocal process, a right vocal process, and an anterior commissure;

receiving a larynx image, a plurality of larynx images captured frame-by-frame, or a larynx video that is captured when vocal folds are in a phonating state;

extracting at least one glottis image from the larynx image, the plurality of larynx images, or the larynx video by the deep learning object detection software;

recognizing a membranous glottal gap in the at least one glottis image by the deep learning image recognition and segmentation software and outputting at least one membranous glottal gap filter corresponding to the at least one glottis image by the deep learning image recognition and segmentation software; and performing image processing of edge detection and image inpainting on the at least one membranous glottal gap filter to clearly outline a membranous glottal gap in the at least one membranous glottal gap filter and obtaining a medical parameter of a plurality of vocal fold anatomies from the clearly outlined membranous glottal gap in the at least one membranous glottal gap filter;

wherein during recognizing the membranous glottal gap in the at least one glottis image, the at least one glottis image is compressed to the at least one glottis image in small size at first; then the deep learning image recognition and segmentation software recognizes the membranous glottal gap in the at least one glottis image in small size and outputs the at least one membranous glottal gap filter in small size corresponding to the at least one glottis image in small size; the at least one membranous glottal gap filter in small size is restored to the at least one membranous glottal gap filter in original size to be output for subsequently performing image processing of edge detection and image inpainting.

2. The method as claimed in claim 1, wherein during obtaining the medical parameter, the medical parameter obtained is a normalized membranous glottal gap area; a membranous glottal gap area of the at least one glottis image is calculated from the clearly outlined membranous glottal gap; a vocal fold length is obtained from the same clearly outlined membranous glottal gap; the vocal fold length is a straight-line distance from the left vocal process to the anterior commissure or from the right vocal process to the anterior commissure; the normalized membranous glottal gap area is calculated from the membranous glottal gap area and the vocal fold length.

3. The method as claimed in claim 1, wherein during obtaining the medical parameter, the medical parameter obtained is an amplitude of vocal fold vibration; the amplitude of vocal fold vibration is a longest distance from a linkage of the left vocal process or the right vocal process and the anterior commissure during vocal fold adduction to a side edge of the membranous glottal gap in a direction perpendicular to the linkage.

4. The method as claimed in claim 2, wherein after obtaining the medical parameter, the method further comprises preparing a graph with a horizontal axis of a capturing time or a frame order and a vertical axis of the normalized membranous glottal gap area.

* * * * *